United States Patent [19]

Nozomi et al.

[11] Patent Number: 5,338,633

[45] Date of Patent: Aug. 16, 1994

[54] ELECTROPHOTOGRAPHIC PHOTORECEPTOR

[75] Inventors: Mamoru Nozomi; Sumiko Watabe; Ryoko Aso, all of Yokohama, Japan

[73] Assignee: Mitsubishi Kasei Corporation, Tokyo, Japan

[21] Appl. No.: 886,845

[22] Filed: May 22, 1992

[30] Foreign Application Priority Data

May 23, 1991 [JP] Japan ................................. 3-118766
Apr. 28, 1992 [JP] Japan ................................. 4-110248

[51] Int. Cl.$^5$ .............................................. G03G 5/06
[52] U.S. Cl. ........................................ 430/59; 430/73; 430/74; 430/78
[58] Field of Search ..................... 430/56, 58, 59, 73, 430/74, 76, 78, 79

[56] References Cited

U.S. PATENT DOCUMENTS 4,665,000  5/1987  Tokolu et al. ........................ 430/85
5,158,850 10/1992  Sasaki et al. ........................ 430/71

OTHER PUBLICATIONS

Patent Abstracts of Japan, vol. 12, No. 252(C-512){3099}, Jul. 15, 1988, & JP-A-63-39842, Feb. 20, 1988, K. Yamataka, et al., "Bis (4-Diphenylaminophenyl)Ether and Production Thereof" Abstract only.
Patent Abstracts of Japan, vol. 7, No. 146(P-206){1291}, Jun. 25, 1983, & JP-A-58-58551, Apr. 7, 1983, Y. Takei, et al., "Electrophotographic Receptor" Abstract only.

*Primary Examiner*—Marion E. McCamish
*Assistant Examiner*—Rosemary Ashton
*Attorney, Agent, or Firm*—Oblon, Spivak, McClelland, Maier & Neustadt

[57] ABSTRACT

An electrophotographic photoreceptor comprising an electrically conductive substrate and a photoconductive layer formed thereon, wherein said photoconductive layer contains a compound of the formula ( I ):

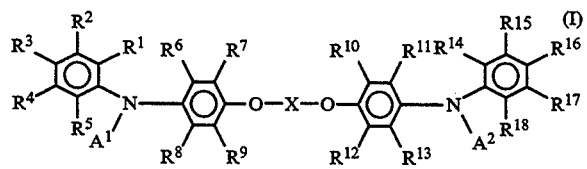

wherein $R^1$ to $R^{18}$ are respectively and independently a hydrogen atom, a halogen atom, a saturated or unsaturated aliphatic hydrocarbon group, an aromatic hydrocarbon group, an alkoxy group, an aryloxy group, a dialkylamino group or a diarylamino group, wherein the aliphatic hydrocarbon group, the aromatic hydrocarbon group, the alkoxy group, the aryloxy group, the dialkylamino group and the diarylamino group may have substituents, X is a bivalent hydrocarbon group which may have substituents, each of $A^1$ and $A^2$ is a saturated or unsaturated aliphatic hydrocarbon group or an aromatic hydrocarbon group, or is bonded to $R^5$ or $R^{18}$ of the adjacent phenyl group to form a nitrogen-containing heterocyclic ring, wherein the aliphatic hydrocarbon group, the aromatic hydrocarbon group and the nitrogen-containing heterocyclic ring may have substituents.

30 Claims, No Drawings

ELECTROPHOTOGRAPHIC PHOTORECEPTOR

The present invention relates to an electrophotographic photoreceptor. More particularly, it relates to a highly sensitive high performance electrophotographic photoreceptor.

In recent years, the electrophotographic technology has been widely used not only in the field of copying machines but also in the field of various printers, since it is thereby possible to obtain high quality images instantaneously. With respect to the photoreceptor which is a key to the electrophotographic technology, an inorganic photoconductor such as selenium, an arsenic-selenium alloy, cadmium sulfite or zinc oxide has heretofore been used as the photoconductive material, and recently, a photoreceptor has been developed in which an organic photoconductive material having such a merit that film-forming is easy without pollution and the production is easy, is used.

Among organic photoreceptors, a so-called laminated photoreceptor has been developed in which a carrier generation layer (i.e. a layer for generating electric charge carriers) and a carrier transport layer (i.e. a layer for transporting electric charge carriers) are laminated, and has been the main object of recent research activities.

The laminated photoreceptor has various advantages such that a highly sensitive photoreceptor can be obtained by a combination of a highly effective carrier generating material and a highly effective carrier transporting material, materials can be selected within wide ranges whereby a photoreceptor having a high level of safety can be obtained, and the productivity in coating is high whereby this photoreceptor is advantageous also from the viewpoint of production costs. Thus, it has a high possibility that it will be the main product among photoreceptors, and is being researched and developed intensively.

However, a laminated photoreceptor which has been actually developed has various problems such that from the viewpoint of electrical characteristics, the photosensitivity is inadequate, the residual potential is high, the photoresponse is poor, the chargeability decreases during the repeated use, the residual potential accumulates, the sensitivity tends to change, and thus it can hardly be regarded as having adequate properties. Especially, it is widely desired to develop a highly sensitive photoreceptor so that it can be used for a high speed copying machine or printer. In the case of the laminated photoreceptor, the photosensitivity of the photoreceptor is deeply related with e.g. the carrier generation efficiency due to light absorption by the carrier generating material, the carrier injection efficiency from the carrier generating material to the carrier transporting material and the carrier transporting efficiency in the carrier transport layer. Among them, it depends largely on the performance of the carrier generating material. However, at the same time, it is very important to increase the performance of the carrier transporting material for the improvement of the sensitivity- Further, the residual potential often creates a problem in the development of an organic photoreceptor and is a substantial factor of hindering the printing resistance. Several factors are conceivable as causes for the residual potential. Among them, the most influential one is believed to be impurities present in the carrier transport layer. As such impurities, those inherently present in the composition, those produced by corona discharge or decomposition products formed upon repeated exposure to image-forming light or to the light of a destaticizing lamp, or to an external light during the maintenance, are conceivable.

Namely, such impurities are believed to serve as traps and capture carriers to form an immobile spatial charge, which constitutes the residual potential. Among them, the impurities inherently present in the composition are believed to be most influential. From an actual study, it has been found that the impurities contained in the carrier transport material are particularly substantially influential over the residual potential. Namely, it is believed that to obtain a carrier transport material having a high purity is one of the essential conditions for developing a photoreceptor of high performance. However, conventional carrier transporting materials such as those disclosed in e.g. U.S. Pat. No. 3,180,730, Japanese Examined Patent Publications No. 153469/1979 and No. 54099/1980 and Japanese Unexamined Patent Publication No. 190864/1990, are produced by rather complicated production routes, whereby various impurities are produced and contained during the reactions, and many of them require repeated purification of high levels.

Under these circumstances, the present inventors have conducted extensive researches for a carrier transport material which shows a high photosensitivity and a sufficiently low residual potential and which at the same time can simply be synthesized and purified. As a result, they have found that a compound having a certain specific triphenyl amine structure shows excellent properties. The present invention has been accomplished on the basis of this discovery.

Thus, the present invention provides an electrophotographic photoreceptor comprising an electrically conductive substrate and a photoconductive layer formed thereon, wherein said photoconductive layer contains a compound of the formula (I):

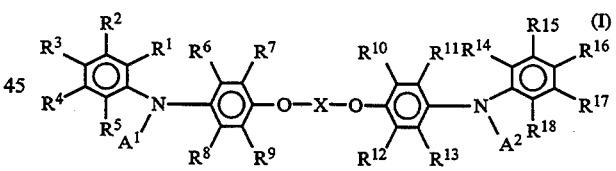

wherein $R^1$ to $R^{18}$ are respectively and independently a hydrogen atom, a halogen atom, a saturated or unsaturated aliphatic hydrocarbon group, an aromatic hydrocarbon group, an alkoxy group, an aryloxy group, a dialkylamino group or a diarylamino group, wherein the aliphatic hydrocarbon group, the aromatic hydrocarbon group, the alkoxy group, the aryloxy group, the dialkylamino group and the diarylamino group may have substituents, X is a bivalent hydrocarbon group which may have substituents, each of $A^1$ and $A^2$ is a saturated or unsaturated aliphatic hydrocarbon group or an aromatic hydrocarbon group, or is bonded to $R^5$ or $R^{is}$ of the adjacent phenyl group to form a nitrogen-containing heterocyclic ring, wherein the aliphatic hydrocarbon group, the aromatic hydrocarbon group and the nitrogen-containing heterocyclic ring may have substituents.

Now, the present invention will be described in detail with reference to the preferred embodiments.

The photoconductive layer used in the present invention is formed on an electrically conductive support or substrate.

As such an electrically conductive support, a metal material support such as aluminum, stainless steel, copper or nickel, or an insulating support such as polyester film or paper, having a conductive layer of e.g. aluminum, copper, palladium, tin oxide or indium oxide formed on its surface, is used.

A conventional barrier layer of the type commonly employed in this field, may be provided between the electrically conductive support and the photoconductive layer.

As the barrier layer, an inorganic layer such as an anodized aluminum film, aluminum oxide or aluminum hydroxide, or an organic layer of e.g. polyvinyl alcohol, casein, polyvinyl pyrrolidone, polyacrylic acid, cellulose, gelatin, starch, polyurethane, polyimide or polyamide, may be used.

The photoconductive layer may be the one wherein a carrier generation layer and a carrier transport layer are laminated in this order, or the one wherein such layers are laminated in a reversed order, or may be of a so-called dispersion type wherein particles of a carrier generating material are dispersed in a carrier transport medium.

In the case of a laminated photoconductive layer, as the carrier generating material to be used for the carrier generation layer, selenium or its alloy, arsenic-selenium, cadmium sulfide, zinc oxide or other inorganic photoconductive material, or various organic photoconductive materials such as phthalocyanine, an azo dye, quinacridone, a polycyclic quinone, a pyrylium salt, a thiapyrylium salt, indigo, thioindigo, anthanthrone, pyranthrone or cyanine, may be used.

Among them, metal free phthalocyanine, a phthalocyanine having a metal or its oxide or chloride, such as copper indium chloride, gallium chloride, tin, oxytitanium, zinc or vanadium, coordinated, or an azo pigment such as a monoazo, bisazo, trisazo or polyazo pigment, is preferred.

The carrier generation layer may be a dispersed layer wherein fine particles of such a material is bound by a binder resin such as a polyester resin, a polyvinyl acetate, a polyacrylate, a polymethacrylate, a polycarbonate, a polyvinyl acetoacetal, a polyvinyl propional, a polyvinyl butyral, a phenoxy resin, an epoxy resin, an urethane resin, a cellulose ester or a cellulose ether. In such a case, the carrier generating material is used usually in an amount of from 30 to 500 parts by weight per 100 parts by weight of the binder resin, and the film thickness is usually from 0.1 to 2 μm, preferably from 0.15 to 0.8 μm. Further, the carrier generation layer may further contain various additives such as a leveling agent to improve the coating property, an antioxidant and a sensitizing agent, as the case requires. Further, the carrier generation layer may be a film formed by vapor deposition of the above carrier generating material.

The carrier transport layer is composed essentially of the compound of the formula (I) and a binder resin.

In the formula, each of $R^1$ to $R^{18}$ is which are independent of one another, is a hydrogen atom; a halogen atom; a saturated aliphatic hydrocarbon group such as a methyl group, a propyl group or an octyl group; an unsaturated aliphatic hydrocarbon group such as an allyl group or an isopropenyl group; an aromatic hydrocarbon group such as a phenyl group or a biphenylene group; an alkoxy group such as a methoxy group, an ethoxy group or a butoxy group; an aryloxy group such as a phenoxy group or a benzyloxy group; a dialkylamino group such as a diethylamino group or a diisopropylamino group; a diarylamino group such as a dibenzylamino group or a diphenylamino group, wherein the saturated or unsaturated aliphatic hydrocarbon group, the aromatic hydrocarbon group, the alkoxy group, the aryloxy group, the dialkylamino group and the arylamino group may, respectively, have substituents.

X is a bivalent hydrocarbon residue such as a methylene group, a propylene group, a xylylene group, a cyclohexylene group, a vinylene group or a phenylene group, and such a bivalent hydrocarbon residue may have substituents such as halogen atoms, hydroxyl groups, saturated or unsaturated hydrocarbon groups, alkoxy groups, aryloxy groups, dialkylamino groups or diarylamino groups. X is preferably an alkylene group of not more than 5 carbon atoms, an alkenylene group of not more than 5 carbon atoms, or a xylylene group.

Each of $A^1$ and $A^2$ which are independent of each other, is a saturated or unsaturated aliphatic hydrocarbon group such as a methyl group, an ethyl group, a propyl group, an allyl group or a propenyl group; an aromatic hydrocarbon group such as a phenyl group, a biphenyl group or a naphthyl group; or is bonded to $R^5$ to $R^{18}$ of the adjacent phenyl group to form a nitrogen-containing heterocyclic group such as indoline, indole, carbazole, or benzocarbazole. Each of $A^1$ and $A^2$ is preferably an aromatic hydrocarbon group or is preferably bonded to $R^5$ to $R^{18}$ of the adjacent phenyl group to form a nitrogen-containing heterocyclic group. Particularly preferably, $A^1$ has the following formula (II), and $A^2$ has the following formula (III).

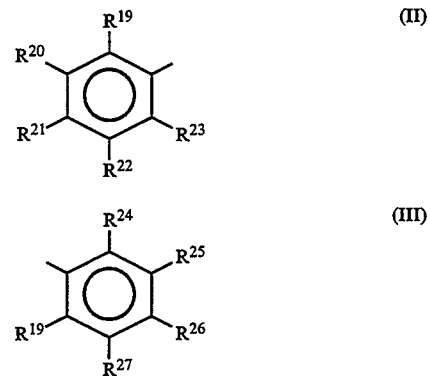

In the above formulas (II) and (III), $R^{19}$ to $R^{28}$ are the same as the definition for $R^1$ to $R^{18}$. Namely, each of $R^{19}$ to $R^{28}$ which are independent of one another is a hydrogen atom; a halogen atom; a saturated aliphatic hydrocarbon group such as a methyl group, a propyl group or an octyl group; an unsaturated aliphatic hydrocarbon group such as an allyl group or an isopropenyl group; an aromatic hydrocarbon group such as a phenyl group or a biphenylene group; an alkoxy group such as a methoxy group, an ethoxy group or a butoxy group; an aryloxy group such as a phenoxy group or a benzyloxy group; a dialkylamino group such as a diethylamino group or a diisopropylamino group; or a diarylamino group such as a dibenzylamino group or a diphenylamino group, wherein the saturated or unsaturated aliphatic hydrocarbon group, the aromatic hydrocarbon group, the alkoxy group, the aryloxy group, the dialkylamino group and the diarylamino group may, respectively, have substituents.

Among the compounds having the formula (I), a preferable compound has a structure wherein $R^{14}$ and $R^1$ the same, $R^{15}$ and $R^2$ being the same, $R^{16}$ and $R^3$ being the same, $R^{17}$ and $R^4$ being the same, $R^{18}$ and $R^5$ being the same, $R^{10}$ and $R^7$ being the same, $R^{11}$ and $R^6$ being the same, $R^{12}$ and $R^9$ being the same, $R^{13}$ and $R^8$ being the same and $A^2$ and $A^1$ being the same.

These preferable compounds can be prepared by reacting a phenolic compound having the following formula (IV) with a dihalogeno compound having the following formula (V), and are expressed by the following formula (VI).

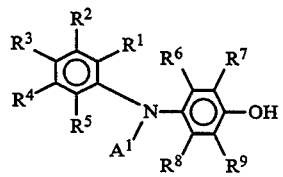 

(IV)　　　　　　　(V)

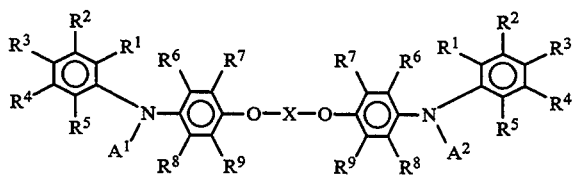

(VI)

In the above formulas (IV) to (VI), $R^1$ to $R^9$ are respectively a hydrogen atom, a halogen atom, a saturated or unsaturated aliphatic hydrocarbon group, an aromatic hydrocarbon group, an alkoxy group, an aryloxy group, a dialkylamino group or a diarylamino group, and the aliphatic hydrocarbon group, the aromatic hydrocarbon group, the alkoxy group, the aryloxy group, the dialkylamino group or the diarylamino group may have a substituent; X is a bivalent hydrocarbon residue which may have a substituent; $A^1$ is a saturated or unsaturated aliphatic hydrocarbon group, an aromatic hydrocarbon group or a nitrogen-containing heterocyclic ring bonded with $R^5$ of the adjacent phenyl group, and these groups may have a substituent; and M is a halogen atom.

Now, typical specific examples of the compound of the formula (I) will be given, but it should be understood that the compound of the formula (I) is by no means restricted to such specific Examples.

In the following formulas, each of $R^1$ to $R^{18}$ is a hydrogen atom unless otherwise specified, and each of $R^1$ and $R^2$ is a phenyl group unless otherwise specified.

When a benzene ring or a cyclohexane ring is present in X, the ortho position of the two bonds or substituents other than hydrogen atoms is identified by o after the chemical formula. Likewise, the meta position and the para position are identified by m and p, respectively.

Typical compounds

| | |
|---|---|
| X: $-CH_2-$ | (1) |
| X: $-CH_2CH_2CH_2-$ | (2) |
| X: $-CH(CH_3)CH(CH_3)-$ | (3) |
| X: $-CH(C_6H_5)CH(C_6H_5)-$ | (4) |
| X: $-CH_2CH(OH)CH_2-$ | (5) |
| X: $-CH_2CH(CH=CH_2)-$ | (6) |
| X: $-CH(C_6H_4Cl)-$, m | (7) |
| X: $-CH=CH-$ | (8) |
| X: $-CH_2-$<br>$R^3$ and $R^{16}$: $-CH_3$ | (9) |
| X: $-CH_2-$<br>$R^3$ and $R^{16}$: $-CH_3$<br>$A^1$ and $A^2$: $-C_6H_5-CH_3$ (bonded at the p-position) | (10) |
| X: $-CH_2-$<br>$R^3$ and $R^{16}$: $-C_6H_5$ | (11) |
| X: $-CH_2-$<br>$R^3$ and $R^{16}$: $-OCH_3$ | (12) |
| X: $-CH_2(C_5H_4)CH_2-$, p | (13) |
| X: $-CH_2(C_6H_4)CH_2-$, m | (14) |
| X: $-CH_2(C_6H_4)CH_2-$, o | (15) |
| X: $-C_6H_4-$, p<br>$R^2$ and $R^{15}$: $-CH_3$ | (16) |
| X: $-C_6H_{10}-$ o | (17) |
| X: $-CH_2-$<br>$R^2$ and $R^{15}$: Cl | (18) |
| X: $-CH_2CH_2CH_2-$<br>$R^3$ and $R^{16}$: $-N(C_2H_5)_2$ | (19) |
| X: $-CH_2-$<br>$R^3$ and $R^{16}$: $-OCH_2(C_6H_5)$ | (20) |
| X: $-CH_2-$<br>$R^3$ and $R^{16}$: $-C_6H_4-N(C_6H_5)_2$ (bonded at the p-position) | (21) |
| X: $-CH_2(C_6H_4)CH_2-$, p<br>$R^3$ and $R^{16}$: $-CH_2CH_2OH$ | (22) |
| X: $-CH_2CH(OCH_3)CH_2-$<br>$R^3$ and $R^{16}$: $-OCH_3$ | (23) |
| X: $-CH_2-$<br>$R^2$ and $R^{16}$: $-C(CH_3)=CH_2$ | (24) |
| X: $-CH_2(C_6H_4)CH_2-$, m<br>$R^2$ and $R^{16}$: $-OC_6H_5$ | (25) |

-continued
Typical compounds

X: —CH$_2$CH$_2$CH$_2$— (26)
R$^2$ and R$^{16}$: —N(C$_6$H$_5$)$_2$
X: —CH$_2$— (27)
R$^{14}$: —CH$_2$CH$_3$
X: —CH$_2$— (28)
R$^{14}$: —CH$_2$—CH=CH$_2$
X: —CH$_2$(C$_6$H$_4$)CH$_2$—, m (29)
R$^{14}$: C$_{10}$H$_7$($\alpha$)
X: —CH$_2$— (30)
A$^1$ and A$^2$: —CH$_3$

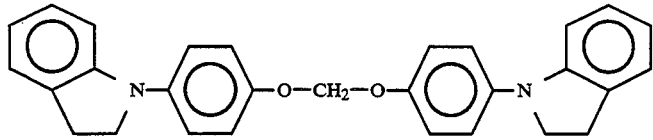
(31)

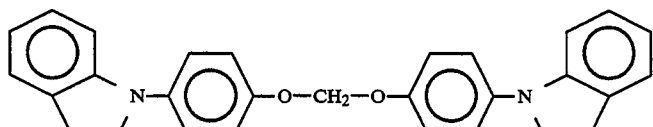
(32)

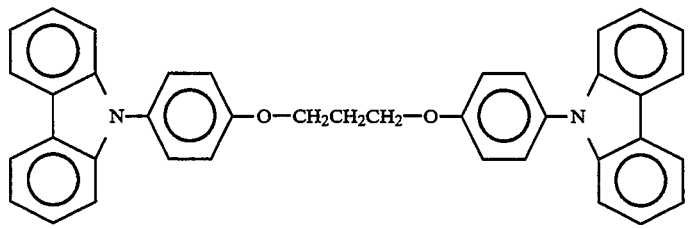
(31)

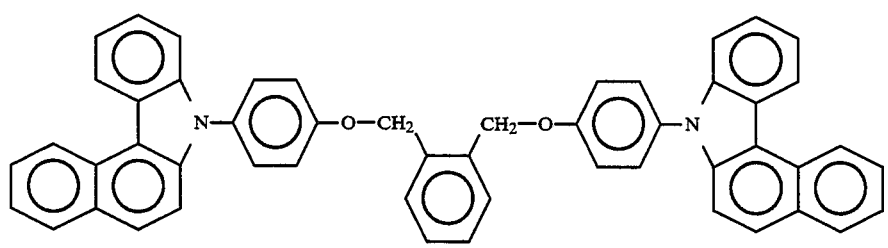
(32)

As the binder resin to be used for the carrier transport layer, a vinyl polymer such as polymethyl methacrylate, polystyrene or polyvinyl chloride, or its copolymer, polycarbonate, polyester, polyester carbonate, polysulfonate, polyimide, or a phenoxy, epoxy or silicone resin, ay be mentioned. Further, partially cross-linked products thereof may be used.

With respect to the proportions of the binder resin and the compound of the formula (I), it is usual that the compound is used within a range of from 30 to 200 parts by weight, preferably from 40 to 150 parts by weight, per 100 parts by weight of the binder resin.

The carrier transport layer may further contain various additives such as an antioxidant and a sensitizer, as the case requires. The thickness of the carrier transport layer is usually from 10 to 60 $\mu$m, preferably from 10 to 45 $\mu$m. As the outermost layer, an overcoat layer made essentially of a conventional thermoplastic or thermosetting polymer, may be formed. Usually, a carrier transport layer is formed on a carrier generation layer. However, the inversed disposition of such layers is possible. For the formation of each layer, a conventional method can be used such that a coating solution obtained by dissolving or dispersing in a solvent a substance to be contained in the layer, is coated sequentially.

In the case of a dispersion-type photoconductive layer, the above described carrier generation material is dispersed in a matrix composed essentially of the binder resin and the compound of the formula (I) in the above described proportions. The particle size in this case is required to be sufficiently small and is preferably not larger than 1 $\mu$m, more preferably not larger than 0.5 $\mu$m. If the amount of the carrier generation material dispersed in the photosensitive layer is too small, no adequate sensitivity will be obtained. On the other hand, if the amount if too much, the chargeabilty tends to be poor, whereby the sensitivity tends to deteriorate. Therefore, the amount of the carrier generation material is preferably within a range of from 0.5 to 50% by weight, preferably from 1 to 20% by weight. The thickness of the photosensitive layer is usually from 5 to 50 $\mu$m, preferably from 10 to 45 $\mu$m. Also in this case, a conventional plasticizer for improving the film-forming property, the flexibility or the mechanical strength, an additive for suppressing the residual potential, a dispersing assistant for improving the dispersion stability, a leveling agent for improving the coating property, a surfactant or other additives such as silicone oil or a fluorine-type oil, may be added.

The electrophotographic photoreceptor of the present invention having a certain specific compound incorporated in the photoconductive layer, has a remarkably high photosensitivity and shows a low residual potential, and there is no substantial accumulation of the residual potential even when repeatedly used. Further, the stability is excellent with little change in the chargeability and sensitivity, whereby the durability is excellent, and is it useful without any problem for a high speed copying machine or printer. Further, when the compound of the present invention is used for the carrier transport layer of a laminated photoreceptor, the transmittance is high even at a short wave length region, whereby it can be used as a photoreceptor for an analogue color copying machine.

Now, the present invention will be described in further detail with reference to Preparation Examples and Working Examples. However, it should be understood that the present invention is by no means restricted by such specific Examples.

PREPARATION EXAMPLES 1 (PREPARATION OF COMPOUND (13))

26. 1 g of p-hydroxytriphenylamine was dissolved in 150 go f dimethylformamide. Then, 4 g of sodium hydroxide and 13.2 g of p-xylyene dirbromie were added thereto, and the mixture was reacted at 70° C. for 3 hours. Water was added to the reaction solution thereby obtained, and the reaction product was extracted with toluene. Then, the toluene solution was washed with a 2N hydrochloric acid aqueous solution and water, and magnesium sulfate was added thereto, followed by drying overnight. The dried product was then concentrated to obtain an oil. The oil was recrystallized from a solvent mixture of toluene/hexane for purification to obtain white crystals having a melting point of 116° C. The yield of this compound was 92%.

PREPARATION EXAMPLE 2 (Preparation of Compound 1))

The desired product of white color was obtained from p-hydroxytriphenylamine and diiodomethane by the same reaction as in Preparation Example 1. The melting point and the yield of this compound were 148° C. and 95%, respectively.

EXAMPLE 1

10 parts by weight of a has azo compound having the following structure was added to 150 parts by weight of 4-methoxy-4-methylpentanone-1, and the mixture was subjected to pulverizing and dispersing treatment by a sand grind mill. A pigment dispersion thus obtained was added to a 1,2-dimethoxyethane solution containing 5% of polyvinylbutyral (manufactured by Denki Kagaku Kogyo K.K., tradename: #6000-C) to obtain a dispersion having a final solid content of 4.0%.

The dispersion thus obtained was coated by means of a wire bar coater on the surface of a polyethylene terephthalate film having aluminum vapor-deposited on the surface, to provide a carrier generation layer having a dry film thickness of 0.4 g/m².

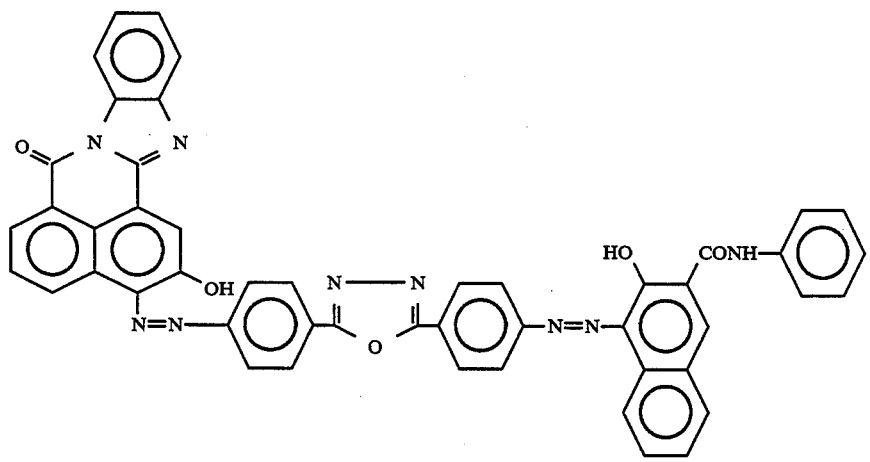

Then, on this carrier generation layer, a solution prepared by dissolving 80 parts by weight of the above compound (1), 4.5 parts by weight of 4'-(2,2'-dicyanovinyl)phenyl 4-nitrobenzoate, 8 parts by weight of 3,5-di-tert-butyl-4-hydroxytoluene and 100 parts by weight of a polycarbonate resin having the following structure, in a solvent mixture of 1,4-dioxane and tetrahydrofuran, was coated by an applicator and then dried at room temperature for 30 minutes and at 125° C. for 15 minutes to provide a carrier transport layer having a dried film thickness of 21 μm. A photoreceptor A thus prepared, was mounted on a tester for photoreceptor properties (EPA-8100, manufactured by Kawaguchi Denki (K.K.) and charged so that the current flowing to the aluminum surface would be 22 μA, followed by exposure and destaticization, whereby the chargeability (Vo) at that time, the decrease of the potential upon expiration of 2 seconds after the initiation of charging (dark damping, DD), the half life of sensitivity to light exposure ($E_{1/2}$) and the residual potential (Vr) were measured. The results are shown in Table 1. As is evident from t he results, the photosensitivity is very high, and the levels of the dark damping and the residual potential are good.

EXAMPLES 2, 3 AND 4

Photoreceptors B, C and D were prepared in the same manner as in Example 1 except that Compounds (13), (14) and (15) were used instead of the Compound (1) used in Example 1, and their properties were evaluated. It is evident from Table 1that each photoreceptor exhibits excellent properties.

TABLE 1

| Photoreceptor | Vo (v) | DD (v) | Vr (v) | E½ (lux · sec) |
| --- | --- | --- | --- | --- |
| A | 634 | 23 | 2 | 0.86 |
| B | 593 | 14 | 6 | 1.27 |
| C | 629 | 21 | 11 | 1.37 |
| D | 637 | 15 | 6 | 1.04 |

EXAMPLE 5

10 parts by weight of oxytitanium phthalocyanine was added to 150 parts by weight of 1,2-dimethoxyethane, and the mixture was subjected to pulverizing and dispersing treatment by a sand grind mill. A pigment dispersion thus obtained was added to a 1,2-dimethoxyethane solution containing 5% of polyvinylbutyral (manufactured by Denki Kagaki Kogyo K.K., tradename: #6000-C) to obtain a dispersion having a final solid content of 4.0%.

The dispersion thus obtained was coated by a wire bar on the surface of a polyethylene terephthalate film having aluminum vapor-deposited on the surface, to provide a carrier generation layer having a dried film thickness of 0.4 g/m².

Then, on the carrier generation layer, a solution prepared by dissolving 90 parts by weight of the above-mentioned Compound (1) and 100 parts by weight of the same polycarbonate resin as used in Example 1 in a solvent mixture of 1,4-dioxane and tetrahydrofuran, was coated by an applicator and then dried at room temperature for 30 minutes and at 1250° C. for 15 minutes to provide a carrier transport layer having a dried film thickness of 17 μm.

The photoreceptor properties of photoreceptor E thus prepared were measured. The results are shown in Table 2. As is evident from the results, the photosensitivity is very high, and the levels of dark damping and the residual potential are good.

EXAMPLE 6

A photoreceptor F was prepared in the same manner as in Example 5 except that Compound (15) was used instead of the Compound (1) in Example 5. The evaluation results are shown in Table 2, from which it is evident that the photosensitivity, the dark damping and the residual potential all show excellent characteristics.

TABLE 2

| Photoreceptor | Vo (v) | DD (v) | Vr (v) | E½ (lux · sec) |
| --- | --- | --- | --- | --- |
| E | 625 | 18 | 6 | 1.05 |
| F | 614 | 25 | 7 | 1.49 |

EXAMPLE 7

The coating solutions for the carrier generation layer and the carrier transport layer prepared in Example 1 were sequentially coated by a dipping method on an aluminum cylinder having a diameter of 80 mm, a length of 340 mm and a wall thickness of 1 mm, to obtain a photoreceptor of a drum shape having a 0.4 g/m² of a charge generation layer and 21 μm of a carrier transport layer. This photoreceptor was mounted on a commercially available analogue color copying machine, and evaluation of the image was conducted by using a color original, whereby an excellent image with sufficient reproduction in each of the red region, the green region and the blue region, was obtained. As is evident from this result, this photoreceptor has a high sensitivity in the three color regions.

As is evident from the foregoing results, the photoreceptor of the present invention has excellent properties.

We claim:

1. An electrophotographic photoreceptor comprising an electrically conductive substrate and a photoconductive layer formed thereon, wherein said photoconductive layer contains a compound of the formula (I):

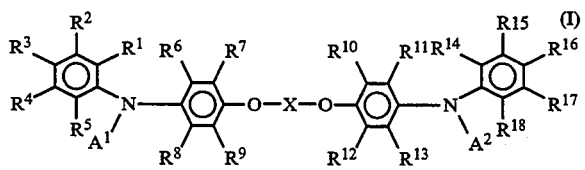

wherein $R^1$ to $R^{18}$ are respectively and independently a hydrogen atom, a halogen atom, a saturated or unsaturated aliphatic hydrocarbon group, an aromatic hydrocarbon group, an alkoxy group, an aryloxy group, a dialkylamino group or a diarylamino group, wherein the aliphatic hydrocarbon group, the aromatic hydrocarbon group, the alkoxy group, the alkoxy group, the dialkylamino group and the diarylamino group may behave substituents, X is a substituted or unsubstituted bivalent hydrocarbon group selected from an alkylene group, an alkenylene group, a cyclohexylene group, a phenylene group, and xylylene, each of $A^1$ and $A^2$ is a saturated or unsaturated aliphatic hydrocarbon group or an aromatic hydrocarbon group, or is bonded to $R^5$ or $R^{18}$ of the adjacent phenyl group to form a nitrogen-containing heterocyclic ring, wherein the aliphatic hydrocarbon group, the aromatic hydrocarbon group and the nitrogen-containing heterocyclic ring may have substituents.

2. The electrophotographic photoreceptor according to claim 1, wherein in the formula (I), $A^1$ is a group having the following formula (II) and $A^2$ is a group having the formula (III):

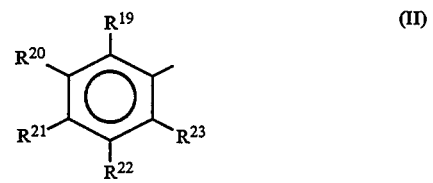

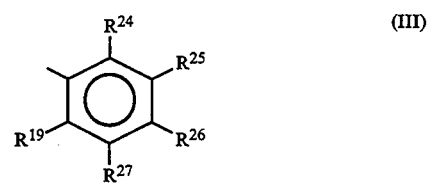

wherein $R^{19}$ to $R^{28}$ are respectively a hydrogen atom, a halogen atom, a saturated or unsaturated aliphatic hydrocarbon group, an aromatic hydrocarbon group, an alkoxy group, an aryloxy group group, a dialkylamino group or a diarylamino group, and the aliphatic hydrocarbon group, the aromatic hydrocarbon group, the alkoxy group, the aryloxy group, the dialkylamino group or the diarylamino group may have a substituent.

3. The electrophotographic photoreceptor according to claim 1, wherein in the formula (I), X is a substituted bivalent hydrocarbon group containing at least one substituent selected from halogens, hydroxyl group, alkoxy group, aryloxy groups dialkylamino groups, diarylamino groups, saturated hydrocarbon groups and unsaturated hydrocarbon groups.

4. The electrophotographic photoreceptor according to claim 1, wherein in the formula (I), $R^{14}$ and $R^1$ are the same, $R^{15}$ and $R^2$ being the same, $R^{16}$ and $R^3$ being the same, $R^{17}$ and $R^4$ being the same, $R^{18}$ and $R^5$ being the same, $R^{10}$ and $R^7$ being the same, $R^{11}$ and $R_6$ being the same, $R^{12}$ and $R^9$ being the same, $R^{13}$ and $R^8$ being the same and $A^2$ and $A^1$ being the same.

5. The electrophotographic photoreceptor according to claim 1, wherein the electrically conductive substrate is a metal material support or an insulating support having a conductive layer formed on its surface.

6. The electrophotographic photoreceptor according got claim 5, wherein the metal material support is at least one member selected from the group consisting of aluminum, stainless steel, copper and nickel.

7. The electrophotographic photoreceptor according to claim 5, wherein the insulating support is a polyester film or paper having at least one conductive layer selected from the group consisting of aluminum, copper, palladium, tin oxide and indium oxide, formed thereon.

8. The electrophotographic photoreceptor according to claim 1, wherein in the formula (I), each of $A^1$ and $A^2$ is a saturated or unsaturated aliphatic hydrocarbon group or is bonded to $R^5$ or $R^{18}$ of the adjacent phenyl group to form a nitrogen-containing heterocyclic ring.

9. The electrophotographic photoreceptor according to claim 1, wherein in the formula (I), X is a substituted or unsubstituted bivalent hydrocarbon selected from $C_1$-$C_5$ alkylenes and $C_1$-$C_5$ alkenylenes.

10. The electrophotographic photoreceptor according to claim 1, wherein the photoconductive layer contains a compound of the formula (I), a charge generating material and a binder resin.

11. The electrophotographic photoreceptor according to claim 10, wherein the photoconductive layer has a thickness of from 5 to 50 μm.

12. The electrophotographic photoreceptor according to claim 10, wherein the photoconductive layer has a thickness of from 10 to 45 μm.

13. The electrophotographic photoreceptor according to claim 10, wherein the binder resin is at least one member selected from the group consisting of a vinyl polymer or its copolymer, a polycarbonate, a polyester, a polyester carbonate, a polysulfonate, a polyimide, a phenoxy resin, an epoxy resin, a silicone rein and a partially cross linked product thereof.

14. The electrophotographic photoreceptor according to claim 10, wherein the photoconductor layer comprises a charge generation layer containing at least a charge generating material and a charge transport layer containing a compound of the formula (I) and a binder resin.

15. The electrophotographic photoreceptor according to claim 14, wherein the charge transport layer has a thickness of from 10 to 60 μm.

16. The electrophotographic photoreceptor according to claim 14, wherein the charge transport layer has a thickness of from 10 to 45 μm.

17. The electrophotographic photoreceptor according to claim 14, wherein the charge generation layer has a thickness of from 0.1 to 2 μm.

18. The electrophotographic photoreceptor according to claim 14, wherein the charge generation layer has a thickness of from 0.15 to 0.8 μm.

19. The electrophotographic photoreceptor according to claim 14, wherein the charge generation layer contains a charge generating material an da binder resin, and the binder resin is at least one member selected from the group consisting of a polyester resin, a polyphenyl acetate, a polyacrylate, a polymethacrylate, a polycarbonate, a polyvinylacetoacetal, a polyvinylpropional, a polyvinylbutyral, a phenoxy resin, an epoxy resin, an urethane rein, a cellulose ester and a cellulose ether.

20. The electrophotographic photoreceptor according to claim 14, wherein the binder resin contained in the charge transport layer is at least one member selected from the group consisting of a vinyl polymer or its copolymer, a polycarbonate, a polyester, a polyester carbonate, a polycarbonate, a polyester, a polyester carbonate, a polysulfone, a polyimide, a phenoxy resin, an epoxy resin, a silicone resin and a partially cross linked product thereof.

21. The electrophotographic photoreceptor according to claim 20 or 13, wherein the vinyl polymer is at least one member selected from the group consisting of a polymethylmethacrylate, a polystyrene and a polyvinyl chloride.

22. The electrophotographic photoreceptor according to claim 10 or 14, wherein the charge generating material is an inorganic photoconductive material.

23. The electrophotographic photoreceptor according to claim 22, wherein the inorganic photoconductive material is at least one member selected from the group consisting of selenium or its alloy, arsenic-selenium, cadmium sulfide and zinc oxide.

24. The electrophotographic photoreceptor according to claim 10 or 14, wherein the charge generating material is an organic photoconductive material.

25. The electrophotographic photoreceptor according to claim 24, wherein the organic photoconductive material is at least one member selected from the group consisting of a phthalocyanine, an azo dyestuff, quinacridone, a polycyclic quinone, a pyrylium salt, a thiapyrylium salt, indigo, thioindigo, anthanthrone, pyranthrone and cyanine.

26. The electrophotographic photoreceptor according to claim 25, wherein the phthalocyanine is at least one member selected from the group consisting of metal free phthalocyanine, a phthalocyanine having a metal coordinate, a phthalocyanine having a metal oxide coordinated and a phthalocyanine having a metal chloride coordinated.

27. The electrophotographic photoreceptor according to claim 26, wherein the metal is at least one member selected from the group consisting of tin, zinc and palladium.

28. The electrophotographic photoreceptor according to claim 26, wherein the metal oxide is oxytitanium.

29. The electrophotographic photoreceptor according to claim 26, wherein the metal chloride is copper indium chloride or gallium chloride.

30. The electrophotographic photoreceptor according to claim 25, wherein the azo dyestuff is at least one member selected from the group consisting of monoazo, bisazo, trisazo and polyazo.

* * * * *